United States Patent [19]

Coleman

[11] Patent Number: 5,358,297
[45] Date of Patent: * Oct. 25, 1994

[54] TWEEZERS WITH HINGED MAGNIFYING GLASS

[76] Inventor: Kenneth J. Coleman, P.O. Box 71, Crystal Lake, Ill. 60014-0071

[*] Notice: The portion of the term of this patent subsequent to Nov. 23, 2010 has been disclaimed.

[21] Appl. No.: 148,949

[22] Filed: Nov. 8, 1993

Related U.S. Application Data

[60] Continuation-in-part of Ser. No. 871,475, Apr. 21, 1992, Pat. No. 5,263,754, and Ser. No. 58,948, May 7, 1993, Pat. No. 5,307,595, which is a division of Ser. No. 871,475, Apr. 21, 1992.

[51] Int. Cl.⁵ ................. A45D 26/00; A61B 17/28
[52] U.S. Cl. .................. 294/99.2; 606/211
[58] Field of Search ............ 294/2, 33, 99.2, 902; 81/4, 6, 7, 7.5, 8; 359/804–812, 818, 819; 606/205–207, 210, 211

[56] References Cited

U.S. PATENT DOCUMENTS

| 1,765,366 | 6/1930 | Crater | 294/99.2 X |
| 1,842,403 | 1/1932 | Hunsaker et al. | 294/99.2 X |
| 2,387,054 | 10/1945 | Brustolon | 294/99.2 X |
| 2,435,741 | 2/1948 | Fleenor | 294/99.2 X |
| 3,510,204 | 5/1970 | Jack | 359/810 |
| 3,955,884 | 5/1976 | Del Pesco | 359/808 X |
| 4,836,596 | 6/1989 | Owen | 294/99.2 |
| 5,263,754 | 11/1993 | Coleman | 294/99.2 |

Primary Examiner—Johnny D. Cherry
Attorney, Agent, or Firm—Mathew R. P. Perrone, Jr.

[57] ABSTRACT

A magnifying arm attached to tweezers has the magnifying glass itself hingedly attached to the arm.

6 Claims, 3 Drawing Sheets

FIG. 4 FIG. 5 FIG. 6
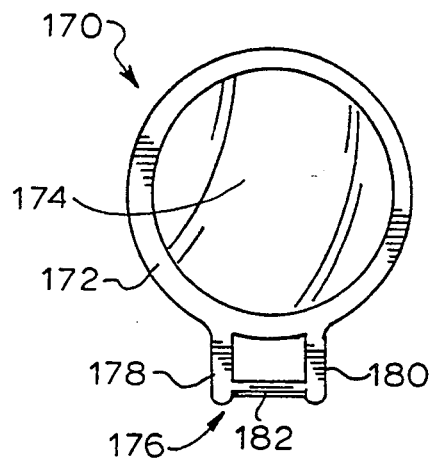
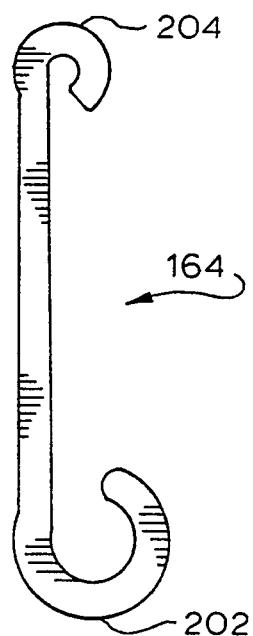
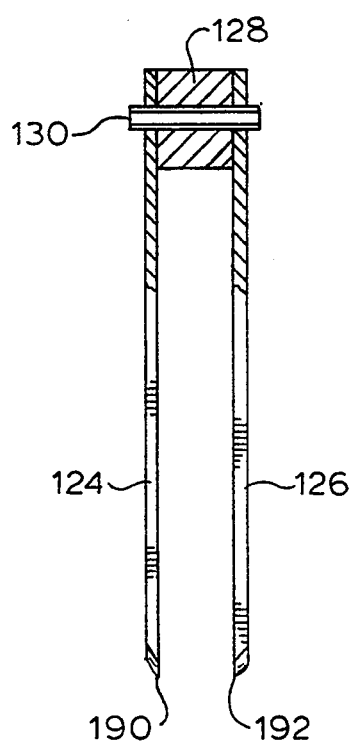
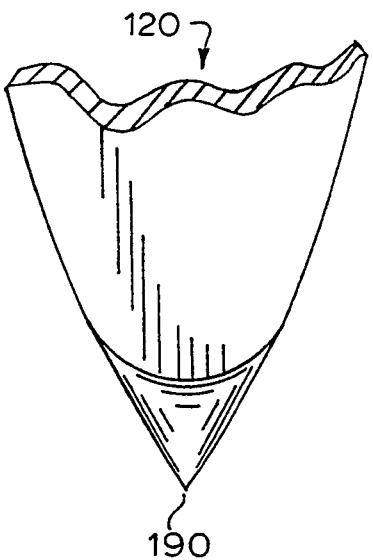
FIG. 7
FIG. 8

5,358,297

TWEEZERS WITH HINGED MAGNIFYING GLASS

CROSS REFERENCE TO RELATED APPLICATIONS

This application is a continuation in part of U.S. patent application Ser. No. 07/871,475 filed Apr. 21, 1992, now U.S. Pat. No. 5,263,754 and U.S. patent application Ser. No. 8/058,948 filed May 7, 1993, now U.S. Pat. No. 5,307,595, both applications being incorporated herein by reference and being filed by Kenneth J. Coleman, the inventor named in this application. U.S. patent application Ser. No. 08/058,948 filed May 7, 1993, is a divisional application of U.S. patent application Ser. No. 07/871,475 filed Apr. 21, 1992.

This invention relates to a combination of tweezers and a magnifying glass and more particularly to a combination of tweezers and a magnifying glass with a moveable glass section.

BACKGROUND OF THE INVENTION

Tweezers are well known in the art. The standard use of tweezers is well set forth in prior patent applications by the same inventor. The prior applications by the inventor is described as use of barbed tweezers and a magnifying glass for viewing the area in which the barbed tweezers are being used.

This magnifying glass assists the gripping of a foreign object in the desired area and the removing of the undesirable foreign object from the skin. The magnifying glass being positioned over the points of the tweezers provides for this very useful purpose in the particular matter. The area being accessed by the tweezers can now be viewed more clearly through the magnifying glass and with much greater efficiency.

However, sometimes it is desirable to move the magnifying glass out of the way without moving the entire arm, on which it is mounted, out of the way. Having found this desired aspect of a tweezers and magnifying glass combination, it is necessary to modify of the prior device to achieve the desired results. Nothing is currently available to meet these important criteria.

SUMMARY OF THE INVENTION

Among the many objectives of the invention is to provide an improved pair of tweezers capable of gripping a desired object with a magnifying glass positioned thereover for viewing of the object.

It is a further objective of this invention to provide tweezers having a magnifying glass secured thereto with a movable glass.

A still further object of this invention is to provide tweezers and a magnifying glass with greater flexibility.

These and other objectives of the invention (which other objectives become completely clear by considering the specification, claims and drawings as a whole) are met by providing tweezers with a magnifying arm wherein the magnifying glass itself is hingedly attached to the arm.

BRIEF DESCRIPTION OF THE DRAWINGS

FIG. 4 depicts the magnifying glass mount 176.

FIG. 5 depicts a side view of tweezers arm 124.

FIG. 6 depicts a side view of magnifying arm 164.

FIG. 7 depicts an assembly of the tweezers 100 in partial cross-section.

FIG. 8 depicts a magnified view of first barbed end 190 of tweezers 120.

Throughout the figures of the drawings where the same part appears in more than one figure the same number is applied thereto.

DESCRIPTION OF THE PREFERRED EMBODIMENTS

The tweezers of this invention include a first arm mounted parallel to a second arm. Between the arms at a fixed end of each arm is a spacing device. Each arm is secured to the spacing device and mounted on an opposite side of the spacing device. Each arm has a barbed tip and a rounded end oppositely disposed from the barbed tip.

A magnifying arm has a spacing clip, which is clipped over the spacing device. At the opposing end of the magnifying arm and opposite the spacing clip is a glass clip which receives a magnifying glass. In this fashion, by slipping the mount for the magnifying glass into the glass clip, the glass may move freely about the glass clip.

Figure 1:
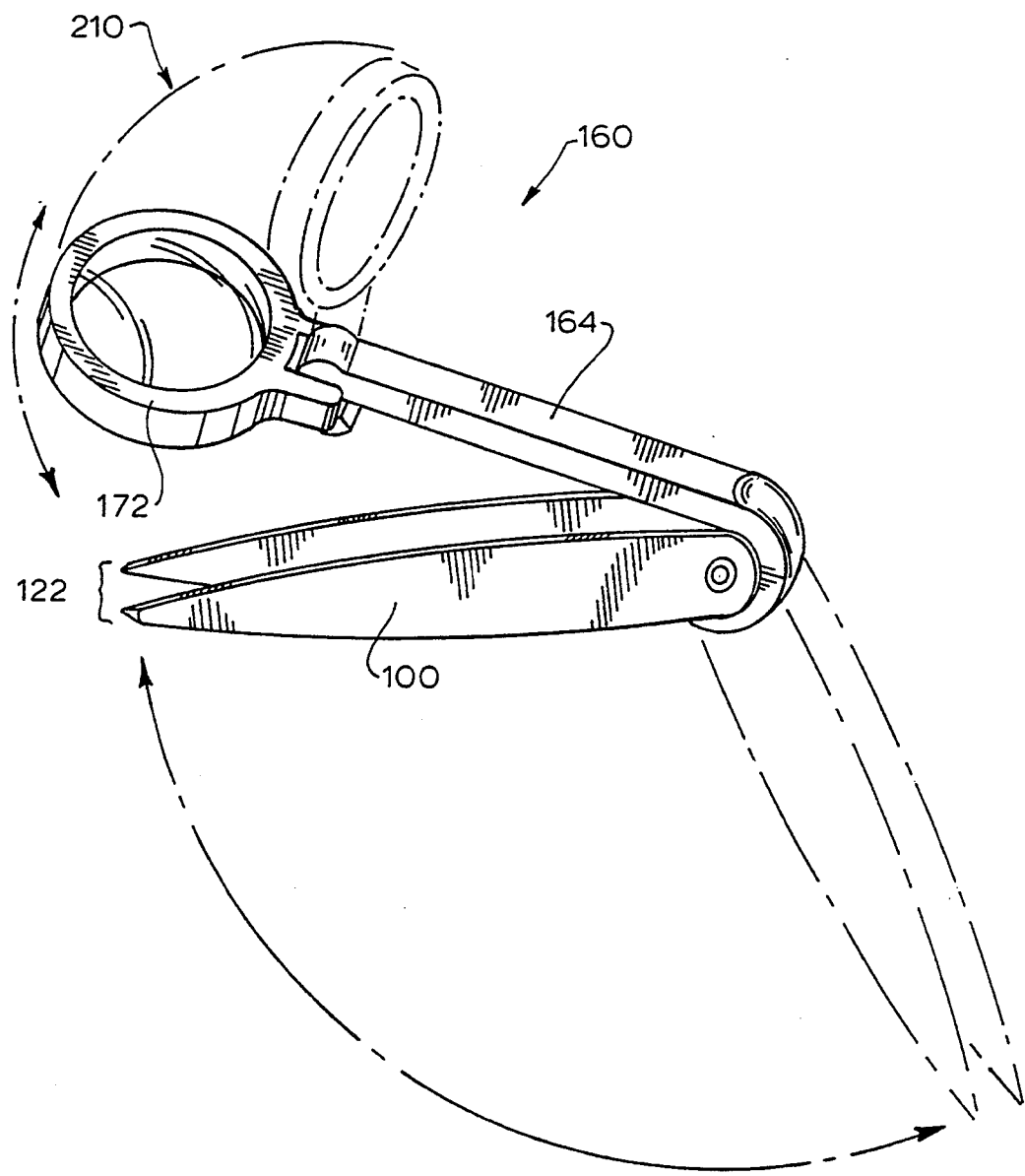
FIG. 1 depicts a perspective view of the tweezers 100 with magnifying glass assembly 160 of this invention.
Figure 2:
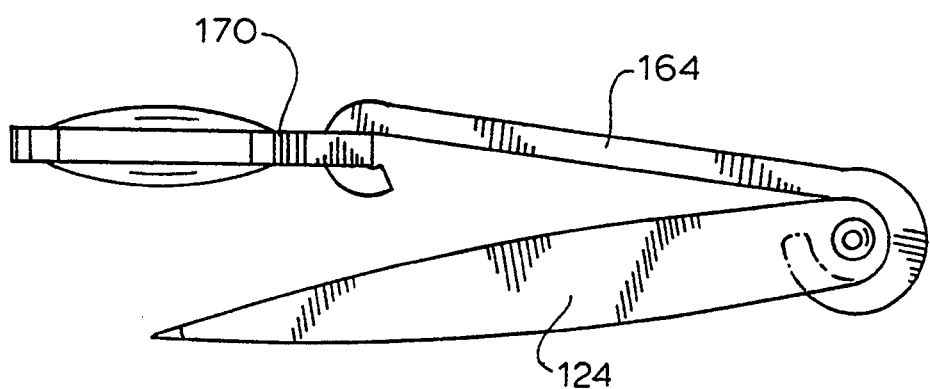
FIG. 2 depicts a side view of FIG. 1.

Referring now to FIG. 1 and FIG. 2, the tweezers 100 and a magnifying glass assembly 160 are combined. A magnifying arm 164 of magnifying glass assembly 160 is movably mounted on tweezers 100. The magnifying glass assembly 160 includes a glass mount 170 movably mounted on the magnifying arm 164.

Figure 3:
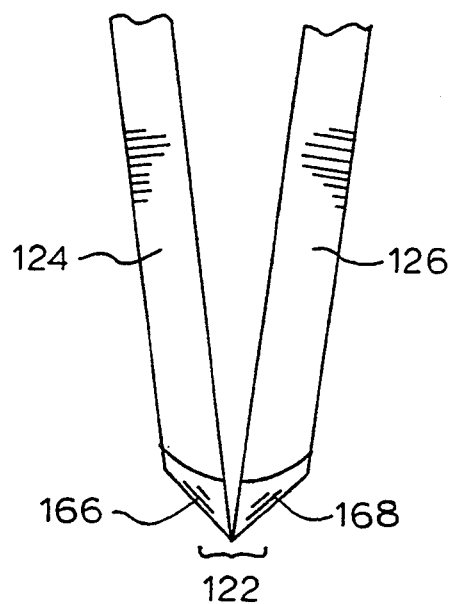
FIG. 3 depicts a perspective view of the tip 122 of tweezers 100.

Referring now to FIG. 3, FIG. 7 and FIG. 8, the tweezers 100 have a tip 122 formed by first barbed end 190 of first arm 124 and second barbed end 192 of second arm 126. Spacer 128 separates first conical shape 166 and second conical shape 168 until it is desired to squeeze the flexible arms (that is first arm 124 and second arm 126) together and form tip 122. First conical shape 166 and second conical shape 168 terminate in first barbed end 190 and second barbed end 192, respectively, to form tip 122.

With FIG. 4, it can be seen that the glass mount 170 has a rim 172 with a glass 174 mounted therein. On the rim of the glass mount 170 is a slot member 176. Slot member 176 has a plurality of component members including a first arm 178 and a second arm 180 with a bar 182 joining the arm at a position spaced apart from the rim 172.

FIG. 5 and FIG. 7 depict the tweezers 100 having a first arm 124 and second arm 126 secured to spacer 128. A rivet 130 is the preferred securing means.

In FIG. 6, the magnifying arm 164 has a spacer clip 202, which fits around the spacer 128 of the tweezers 100. Oppositely disposed from the spacer clip 202 is a glass clip 204. Spacer clip 202 is snap fitted over spacer 128.

Glass clip 204 fits over the bar 182 of glass mount 170. In this fashion, between the spacer clip 202 and the bar 178, the glass mount 170 and the rim 172 with glass 174 can move freely in an arc 210 (shown in phantom in FIG. 1). Such fittings are usually accomplished with a snap fitting due to the flexibility of material (such as plastic) from which the magnifying arm 164 is made.

This application—taken as a whole with the specification, claims, abstract, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this method and apparatus can become clear to a person having ordinary skill in this particular art. Such modifications are clearly covered by this disclosure.

What is claimed and sought to be protected by Letters Patent of the United States is:

1. In a combination of a tweezers and a magnifying glass for removing a foreign object from skin, wherein:
   a) the tweezers includes a spacer means, and a first arm and a second arm;
   b) the first arm has a first rounded end and a first barbed end oppositely disposed from the first rounded end;
   c) the second arm has a second rounded end and a second barbed end oppositely disposed from the second rounded end;
   d) the first rounded end and the second rounded end are secured to the spacer means;
   e) the first arm and the second arm are flexible;
   f) the first barbed end and the second barbed end are normally spaced apart by the spacer means;
   g) the first barbed end and the second barbed end combine to form a cone shape for a barbed tip;
   h) the barbed tip serves to penetrate the skin, grip, and remove a foreign particle from the skin;
   i) the spacer means is a substantially cylindrical shape;
   j) the substantially cylindrical shape includes a tip side and a bottom side;
   k) the first rounded end is adjacent to the top side;
   l) the second rounded end is adjacent to the bottom side;
   m) the first arm ad the second arm are substantially flat; and
   n) a magnifying means is secured in a pivotal fashion to the spacer means;

the improvement comprising:
   the magnifying means includes an arm having a first end and a second end:
   the first end includes a means for pivotally securing the magnifying means to the spacer means; ad
   the second end includes a means for pivotally securing a magnifying glass to the 2. The combination of a tweezers and a magnifying glass for removing a foreign object from skin as set forth in claim 1, wherein:
   a) the means for pivotally securing the magnifying means to the spacer means includes a spacer clip pivotally mounted on the spacer means; and
   b) the means for pivotally securing a magnifying glass to the arm includes a glass clip for receiving a glass mount.

3. The combination of a tweezers and a magnifying glass for removing a foreign object from skin as set forth in claim 2, wherein:
   a) the glass mount includes a rim to secure the magnifying glass; and
   b) the rim includes a slot member protruding therefrom to be received in the glass clip.

4. The combination of a tweezers and a magnifying glass for removing a foreign object from skin as set forth in claim 3, wherein:
   a) the slot member includes a first member and a second member with a bar; and
   b) the bar joins the first member and the second member at a position spaced apart from the rim.

5. The combination of a tweezers and a magnifying glass for removing a foreign object from skin as set forth in claim 4, wherein the first member and the second member are substantially parallel.

6. The combination of a tweezers and a magnifying glass for removing a foreign object from skin as set forth in claim 5, wherein:
   a) the bar is substantially perpendicular to the first member and the second member; and
   b) the bar receives the glass clip.

* * * * *